(12) United States Patent
Ji (10) Patent No.: US 9,414,966 B2
(45) Date of Patent: Aug. 16, 2016

(54) METAL EARPAD

(71) Applicant: GN Netcom A/S, Ballerup (DK)

(72) Inventor: Sunny Ji, Xiamen (CN)

(73) Assignee: GN Netcom A/S (DK)

( * ) Notice: Subject to any disclaimer, the term of this patent is extended or adjusted under 35 U.S.C. 154(b) by 0 days.

(21) Appl. No.: 14/655,623

(22) PCT Filed: Dec. 20, 2013

(86) PCT No.: PCT/EP2013/077696
§ 371 (c)(1),
(2) Date: Jun. 25, 2015

(87) PCT Pub. No.: WO2014/102191
PCT Pub. Date: Jul. 3, 2014

(65) Prior Publication Data
US 2015/0358712 A1 Dec. 10, 2015

(30) Foreign Application Priority Data

Dec. 28, 2012 (CN) .......................... 2012 1 0584262

(51) Int. Cl.
| | |
|---|---|
| *H04R 5/033* | (2006.01) |
| *A61F 11/14* | (2006.01) |
| *H04R 1/10* | (2006.01) |
| H04R 5/00 | (2006.01) |
| A61F 11/06 | (2006.01) |

(52) U.S. Cl.
CPC .............. *A61F 11/14* (2013.01); *H04R 1/1008* (2013.01)

(58) Field of Classification Search
CPC ......... A61F 11/06; A61F 11/12; A61F 11/14; H04R 1/1008; H04R 5/033
USPC .......... 181/129, 126, 128; 128/864, 866, 867; 381/371, 370; 2/208, 209
See application file for complete search history.

(56) References Cited

U.S. PATENT DOCUMENTS

| | | | | |
|---|---|---|---|---|
| 2,850,012 | A * | 9/1958 | Becker | A61F 11/08 128/864 |
| 3,938,614 | A * | 2/1976 | Ahs | A61F 11/14 128/867 |
| 4,459,707 | A | 7/1984 | Stallings | |
| 4,572,323 | A * | 2/1986 | Randall | A61F 11/14 181/129 |
| 4,581,285 | A * | 4/1986 | Mahefkey, Jr. | B32B 15/08 220/592.21 |
| 4,674,134 | A | 6/1987 | Lundin | |
| 4,989,271 | A * | 2/1991 | Sapiejewski | A61F 11/14 2/209 |
| 5,138,722 | A * | 8/1992 | Urella | A61F 11/14 2/209 |
| 5,456,703 | A * | 10/1995 | Beeuwkes, III | A61F 7/02 607/109 |

(Continued)

FOREIGN PATENT DOCUMENTS

| | | | | |
|---|---|---|---|---|
| AT | | 325693 | 11/1975 | |
| GB | | 2068681 | 8/1981 | |
| WO | WO 2009018677 | A1 * | 2/2009 | .......... H04R 1/1008 |

OTHER PUBLICATIONS

International Search Report for PCT application No. PCT/EP2013/077696 date of mailing Apr. 2, 2014.

*Primary Examiner* — Edgardo San Martin
(74) *Attorney, Agent, or Firm* — Altera Law Group, LLC (57) ABSTRACT

An earpad (1) to provide an interface between an earcup (4) of a headset (7), a headphone (8) or an ear defender (9). The earpad (1) comprises a contact surface (2) contacting the skin (10) of the ear (11) or ear surroundings of the user. The earpad (1) comprises one or more metal members (3, 6, 12, 13, 33) to transfer heat away from the contact surface (2).

17 Claims, 6 Drawing Sheets

(56) References Cited

U.S. PATENT DOCUMENTS

| | | | | |
|---|---|---|---|---|
| 5,660,917 A * | 8/1997 | Fujimori | ............. | H01L 23/3677 165/185 |
| 5,821,468 A * | 10/1998 | Urella | ..................... | A61F 11/14 181/129 |
| 5,851,338 A * | 12/1998 | Pushaw | ..................... | B32B 5/18 156/278 |
| 5,911,314 A * | 6/1999 | Urella | ..................... | A61F 11/14 2/209 |
| 6,788,797 B2 * | 9/2004 | Kim | ..................... | H04R 1/1008 381/309 |
| 6,855,410 B2 * | 2/2005 | Buckley | ..................... | A61F 7/02 2/113 |
| 6,856,690 B1 * | 2/2005 | Skulley | ................ | H04R 1/1008 381/367 |
| 7,077,858 B2 * | 7/2006 | Fletcher | .................... | A61F 7/02 607/104 |
| 8,746,397 B2 * | 6/2014 | Peskar | .................... | A61F 11/14 181/129 |
| 8,910,313 B2 * | 12/2014 | Gordon | ................. | A41D 27/28 2/69 |
| 2005/0089185 A1 * | 4/2005 | Allen | ................... | H04R 1/1008 381/370 |
| 2009/0163984 A1 * | 6/2009 | Robinson | ................. | A61F 7/02 607/114 |
| 2010/0119076 A1 * | 5/2010 | Monk | .................... | A61F 11/14 381/71.6 |
| 2014/0079270 A1 * | 3/2014 | Essabar | ............... | H04R 1/1008 381/370 |
| 2015/0335466 A1 * | 11/2015 | Schoggler | ............... | A61F 11/08 607/109 |

* cited by examiner

METAL EARPAD

TECHNICAL FIELD

The invention relates to an earpad to provide an interface between an earcup of a headset, a headphone or an ear defender, which earpad comprises a contact surface contacting the skin of the ear or ear surroundings of the user.

BACKGROUND ART

Headsets used for two-way communication and audio listening and pure headphones only used for audio listening can be divided into four categories: circumaural, supra-aural, earbud and in-ear headphones.

Circumaural headphones have earpads that encompass the ears. As these headphones completely surround the ear, they can seal very efficiently against external noise.

Supra-aural headphones have earpads that press on the ears, and not around them.

Both circumaural and supra-aural headphones can be provided with open-back earcups or closed-back earcups. The open-back earcups do not block out external noise and audio and leaks audio from the speaker to the surroundings. The closed-back earcups more efficiently blocks out external noise and do not leak audio in any significant amount.

Ear defenders are of a construction similar to the closed-back circumaural headphones, as the main purpose is to block out external noise.

Users of headsets and headphones of the circumaural and supra-aural type and ear defenders often experience discomfort due to build-up of heat in the interface between the earpad and skin of the user. The soft earpad is pressed against the skin of the ear or ear surroundings, and is adapted to the surface whereby heat is more or less prevented from dissipating from the skin. Especially because the earpad normally is a made of foam which has a heat insulating effect. As the earpad often is provided with a cover layer of artificial leather or just soft plastic, air is prevented from cooling the interface between the skin and the earpad. Thus, the ear or ear surroundings may feel warm by the user, whereby he may desire to remove the headset after a short time of use.

Different solutions have been proposed to solve this problem.

U.S. Pat. No. 6,856,690 B (Plantronics) discloses a headset earpad with microcapsules of a material capable of an endothermic phase change at a substantially constant temperature.

U.S. Pat. No. 4,674,134 A (Bilsom AB) discloses an earpad with a sealing ring, which has an outer liquid ring layer, i.e. one intended for engagement against the head, and inwards thereof a foamed plastics ring layer, i.e. towards the juncture with the rest of the earmuff. This ring layer combination s supposed to have good comfort properties while retaining the properties of the sealing ring necessary for sound damping. The liquid layer is supposed to give a "cooling effect".

DISCLOSURE OF INVENTION

It is an object of the invention to provide an earpad with a good cooling effect.

According to the invention, the earpad comprises one or more metal members to transfer heat away from the contact surface. As metal is known as good heat conductor, heat can be transferred away from the skin in an easy way. The metal members may themselves be embodied as resilient members or be resiliently suspended, whereby the earpad may adapt to the ear or ear surroundings and be comfortable for the user to wear over a prolonged time.

The metal members may comprise metal elements on the contact surface.

The earpad may comprise a flexible cover layer.

According to an embodiment, the metal elements are provided as discrete elements on the flexible cover layer.

The flexible cover layer may comprise a metal foil. This foil may be aluminium foil or copper foil.

According to an embodiment, the flexible cover layer comprises a pliable metal mesh.

The metal foil or metal mesh may be in contact with a heat sink, which dissipates heat into the surrounding air.

According to an embodiment, the metal foil or metal mesh on the contact surface, is covered with a thin layer of softer material. This reduces the cooling effect, but may feel softer and more comfortable for the user.

According to an embodiment, the earpad comprises an earpad body comprising body material which is in contact with the metal elements.

The earpad body may comprise metal wool. This will improve the heat conductance away from the contact surface.

According to an embodiment, the flexible cover layer is liquid tight and the earpad body comprises liquid. A liquid-filled earpad may easily adapt to the surface of the ear or ear surroundings.

According to an embodiment, the metal elements are in contact with a metal heat conductors conducting heat away from the metal elements.

The metal heat conductors may be embodied as springs, which can be shortened, when a compressive force is added to the metal element. The springs may also add to the resiliency of the earpad.

According to an embodiment, the metal heat conductors are in contact with a metal heat sink, which dissipates heat into the surrounding air.

BRIEF DESCRIPTION OF THE DRAWINGS

The invention is explained in detail below with reference to the drawing illustrating embodiments of the invention and in which.

MODES FOR CARRYING OUT THE INVENTION

Figure 1:
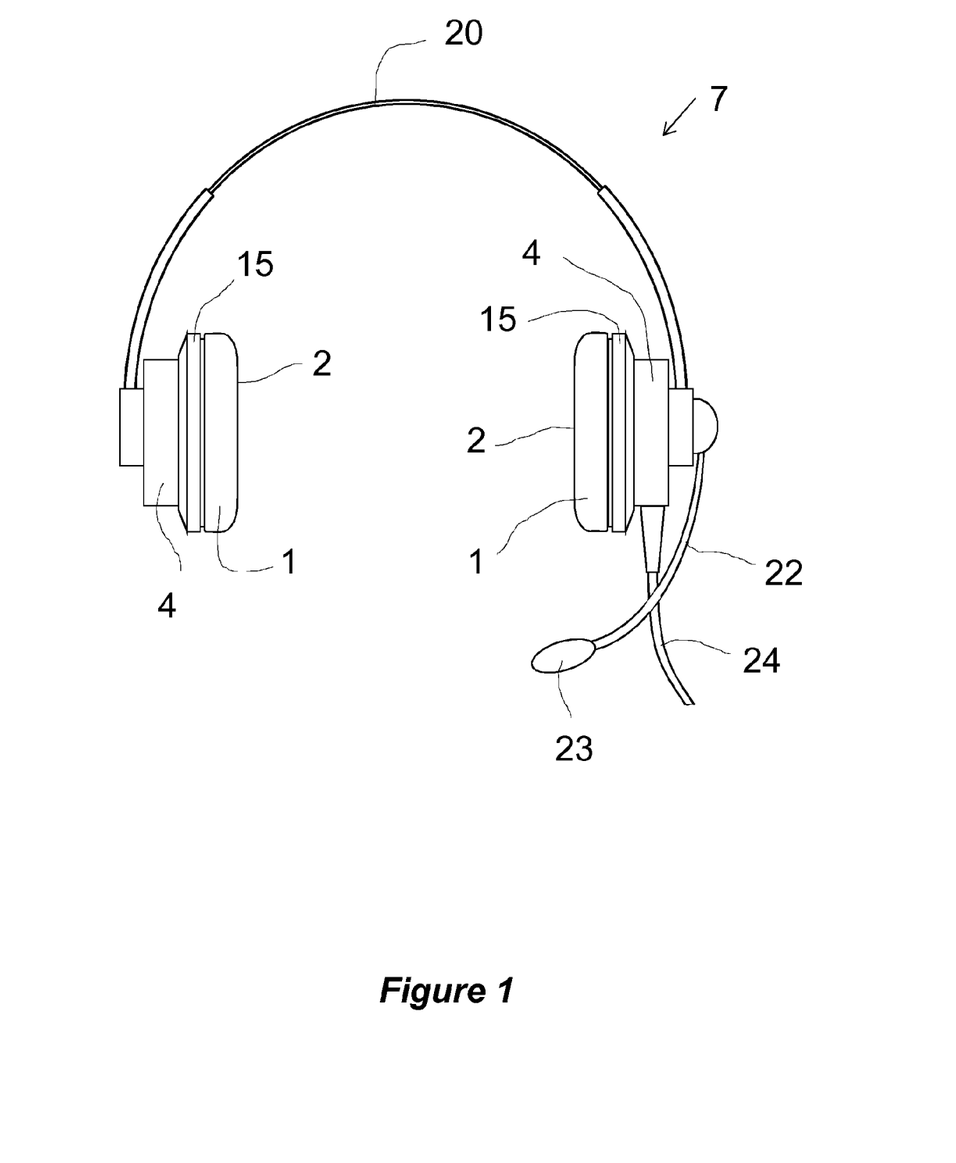
FIG. 1 is a front view of a duo headset incorporating earcups according to the invention.

FIG. 1 is a front view of a duo headset 1. The headset 1 comprises two earcups 4, an adjustable headband 20 interconnecting the two earcups 4, a microphone arm 22 with a microphone 23 and a cord 24 extending from one of the earcups. Each earcup 4 comprises an earpad 1 and a heat sink 15. The inner side of each earpad 1 provides a contact surface 2. The headset 1 is of the supra-aural type, where the earpad 1 is pressing against the ear of the user when worn. Each of the earcups 4 comprises a not shown speaker which provides audio to the ear though an opening in the earpad 1. The earpad 1 is soft whereby it can adapt to the surface of the ear and is comfortable to wear.

Figure 2:
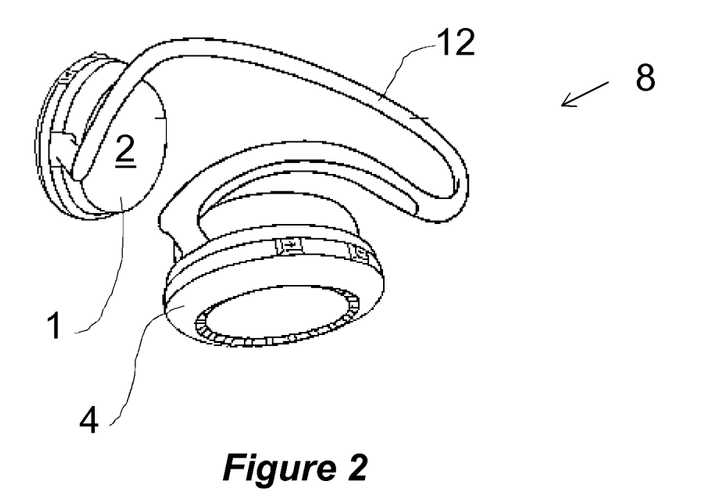
FIG. 2 is a perspective view of a headphone with supra-aural earpads.

FIG. 2 is a perspective view of a headphone 8 of the neckband type. The headphone 8 comprises two earcups 4 and a neckband 22 interconnecting the earcups 4. The earcups 4 are also in this embodiment supra-aural. The headphone is wireless.

Figure 3:
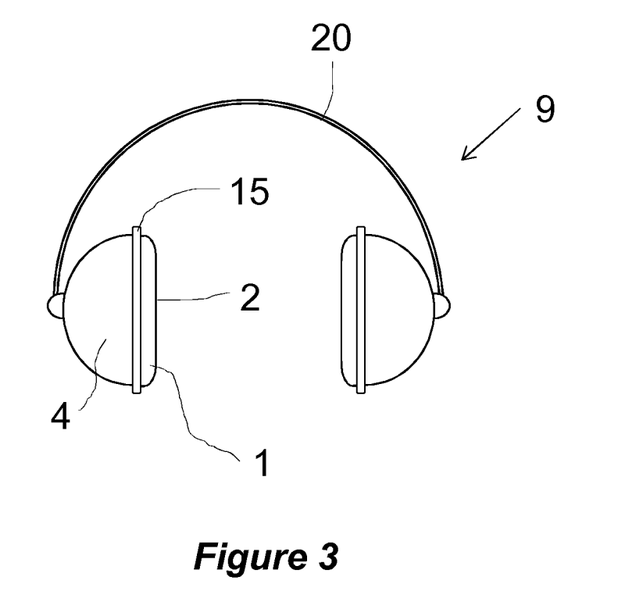
FIG. 3 is a front view of an ear defender.

FIG. 3 is a front view of an ear defender 9 comprising a headband 20 interconnecting two earcups 4, each comprising an earpad 1 with a contact surface 2 and a heat sink 15.

Figure 4:
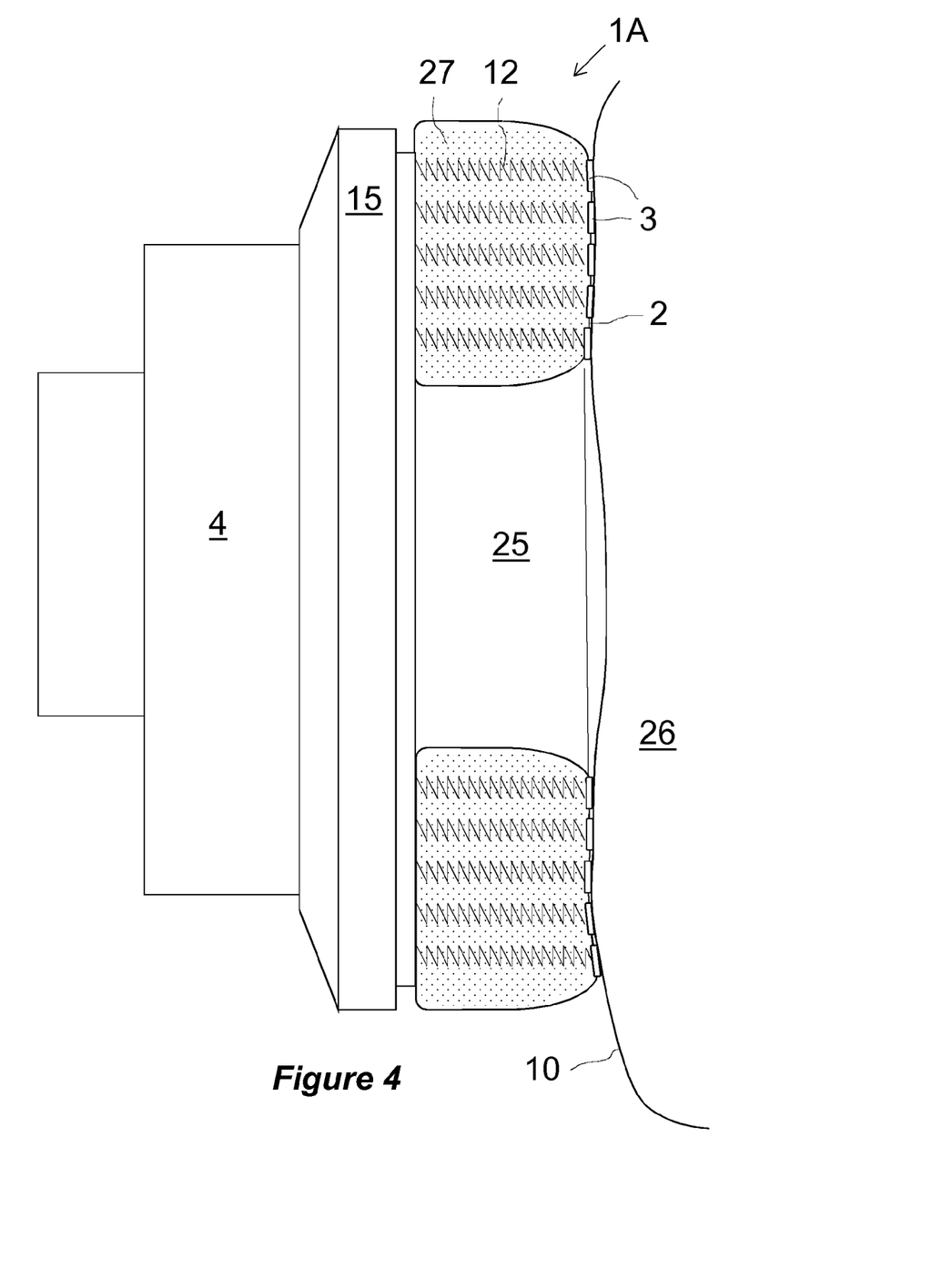
FIG. 4 is a sectional view through a first embodiment of an earpad according to the invention.

FIG. 4 is a sectional view through a first embodiment of an earpad 1A according to the invention. The earpad 1A is ring-shaped, whereby it provides an opening 25 so that audio from the speaker can reach the ear canal of the user. The earpad 1 is pressed against the skin 10 of a user's ear 26. The earpad 1A comprises a flexible cover layer 6, f. ex. soft plastic, which encompasses a space filled with soft foam 27. The contact surface 2 of the flexible cover layer 6 is provided with a plurality of metal elements 3. The earpad 1 is attached to a heat sink 15, and each metal element 3 is thermally connected to the heat sink by means of a metal spring 12. The metal elements 3 are in contact with the skin 10 and heat dissipated from skin 10 is conducted via the metal elements 3 through the metal springs 12 to the heat sink 15, where it is dissipated to the ambient air. The heat sink 15 is made of an aluminium alloy but could be made of other alloys or metals.

Figure 5:
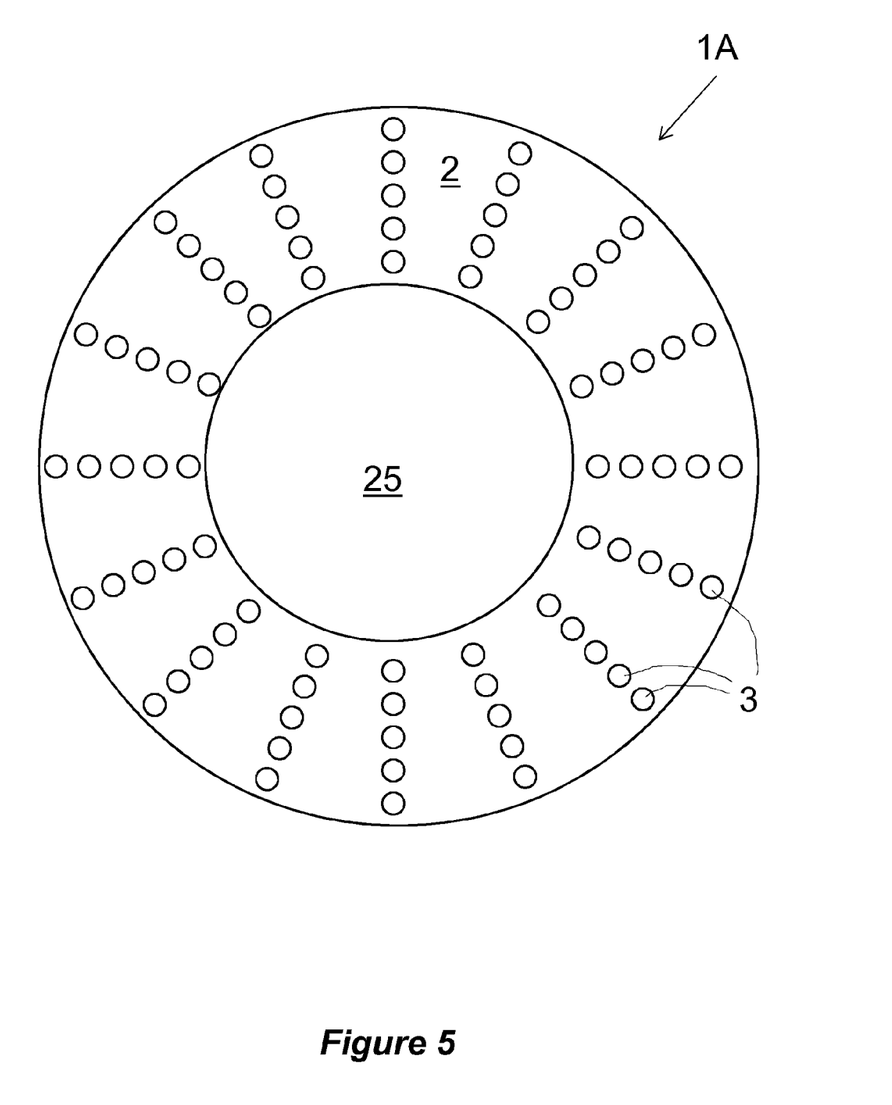
FIG. 5 is a side view of the earpad according to the first embodiment.

FIG. 5 is a side view of the earpad 1A according to the first embodiment. From this view, it is clear that a large number of metal elements 3 are distributed over the contact surface 2 of the ring shaped ear pad 1A. The more metal elements the more efficient heat can be conducted away from the skin. However, the selected number of metal elements 3 is a compromise between cooling effect, weight and softness (comfort).

Figure 6:
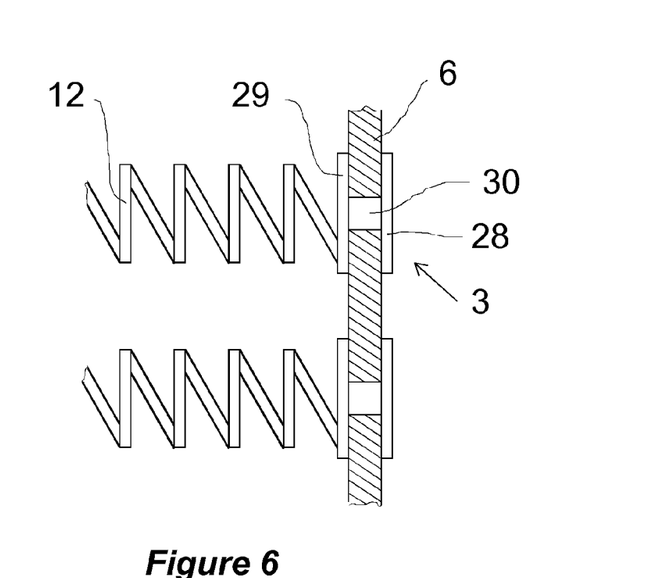
FIG. 6 is an enlarged view of some details of the earpad according to the first embodiment.

FIG. 6 is an enlarged view of some details of the earpad 1A according to the first embodiment. Each metal element 3 comprises an outer part 28, an inner part 29 and an intermediate part 30 connecting the outer part 28 and the inner part 29. The outer part 28 is arranged on the outer side of the cover layer 6 and the inner part 29 is arranged on the inner side of the cover layer 6. The intermediate part 30 has of smaller diameter than the outer and inner parts 28, 29 and extends through a correspondingly sized hole in the cover layer 6, whereby the metal element is secured to the cover layer 6. The inner part 29 of the metal element 29 is directly connected to the metal spring 12.

Figure 7:
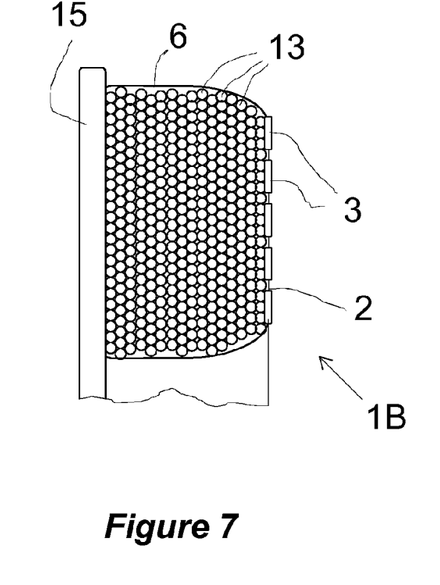
FIG. 7 is a sectional view through an earpad according to a second embodiment.

FIG. 7 is a sectional view through an earpad 1B according to a second embodiment. This earpad 1B comprises a flexible cover layer 6 and metal elements 3 on the contact surface 2 like the first embodiment. The inner space confined by the flexible cover layer 6 is filled with small metal balls 13, which provide heat conductors conducting heat from the metal elements 3 to a heat sink 15. The small metal balls 13 can be displaced in relation to each other, whereby the earpad 1B can adapt to the surface of the ear.

Figure 8:
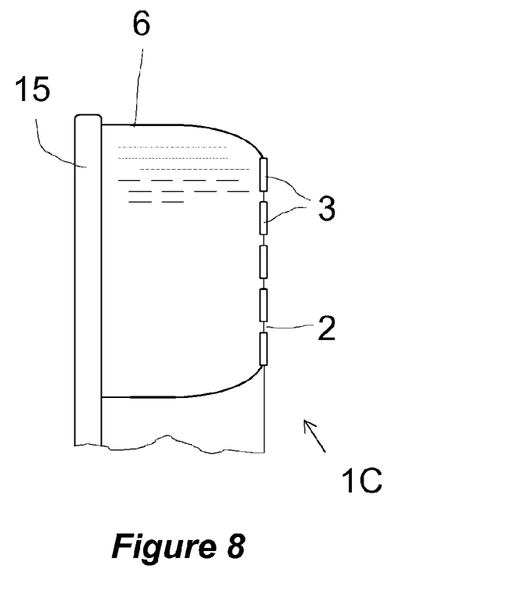
FIG. 8 is a sectional view through an earpad according to a third embodiment.

FIG. 8 is a sectional view through an earpad 1C according to a third embodiment. This embodiment comprises a liquid proof cover layer 6, which together with a heat sink 15 confines a space filled with liquid, which f. ex. can be water based or oil based, and which serves as a heat conductor between the metal elements 3 on the contact surface 2 and the heat sink 15. The metal elements 3 are similar to the metal elements 3 of the first and second embodiments.

Figures 9, 10:
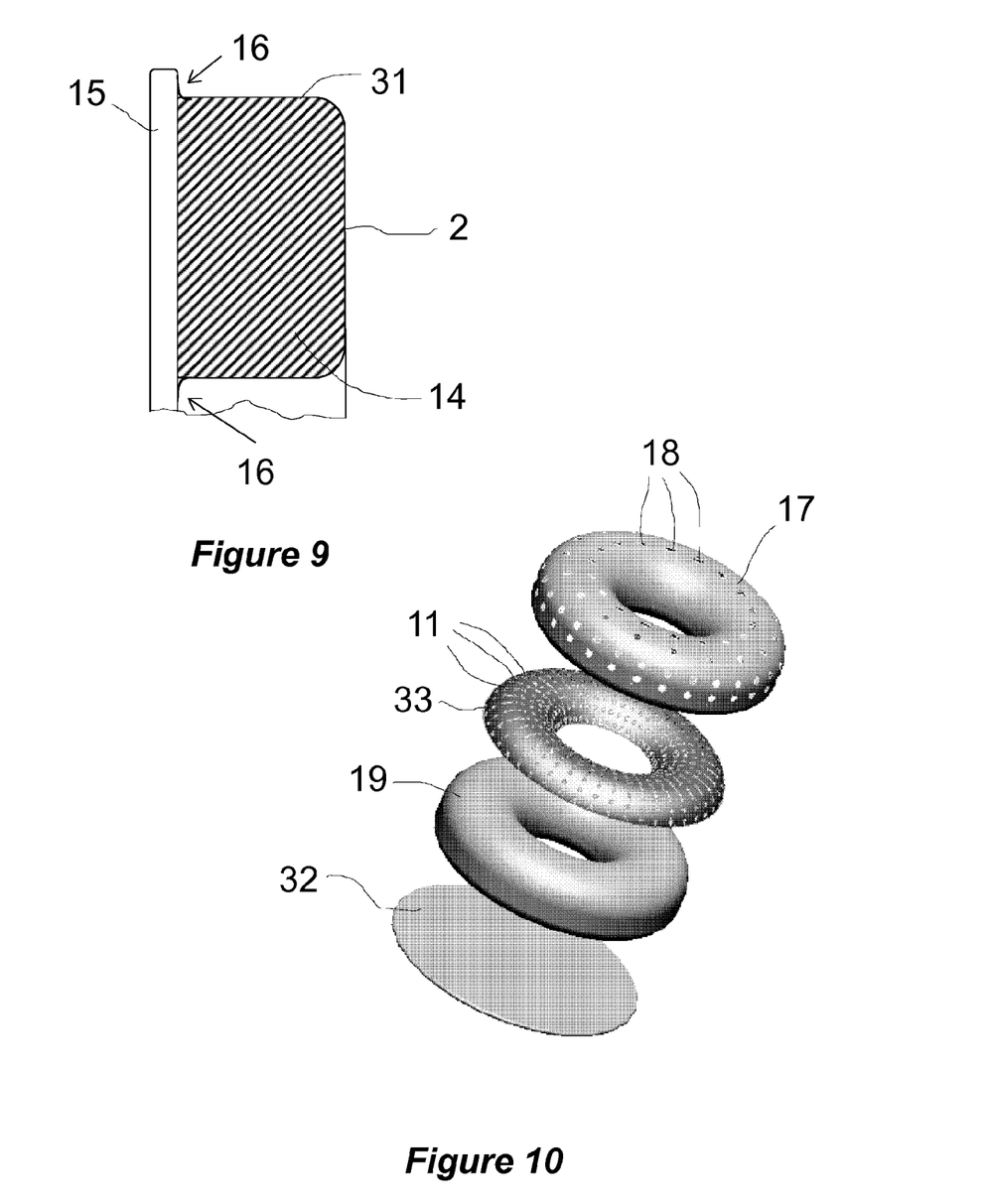
FIG. 9 is a sectional view through an earpad according to fourth embodiment.
FIG. 10 is an exploded view of an earpad according to a fifth embodiment.

FIG. 9 is a sectional view through an earpad 1D according to fourth embodiment, which comprises a heat sink 15 like the previous embodiments. A flexible cover layer consisting of metal braid 31 encloses a metal wool body 14. The metal braid 31 is firmly attached to the heat sink 15 at joints 16 and thermal paste is used to reduce the thermal resistance between the heat sink 15 and the metal braid 31. As the outer cover layer consist of metal braid, there is no need for the metal elements 3 applied in the previous embodiments. The metal wool body 14 is in contact with the inner side of the metal braid and improves the thermal conductivity between the contact surface 2 and the heat sink 15. However, the metal wool body 14 could be replaced by a soft foam body of plastic or rubber. Furthermore, the heat sink 15 could also be omitted as the metal braid 16 itself acts as a heatsink.

FIG. 10 is an exploded view of an earpad 1E according to a fifth embodiment, where an outer thin layer 17 of leather or artificial leather covers a copper mesh 33 on a sponge 19 of plastics or rubber, which again is attached to a base plate 32. The outer layer 18 is very thin in order to reduce the heat resistance between the skin and the copper mesh 33. The copper mesh 33 is also very thin whereby it can flex and adapt itself to the surface of the ear. The outer layer 17 and the copper mesh 33 are provided with air holes 17, 11 in order to ventilate the skin.

As shown in the table below, metals have a much higher thermal conductance than plastic materials, such as PVC and Polypropylene, and dry leather. Therefore, metals and metal alloys are good heat conductors.

| Material | Thermal conductivity W/(mK) |
| --- | --- |
| Silver | 429 |
| Copper | 401 |
| Gold | 310 |
| Aluminium | 205 |
| Nickel | 91 |
| Iron | 80 |
| Stainless steel | 16 |
| PVC | 0.19 |
| Leather, dry | 0.14 |
| Polypropylene | 0.1-0.22 |

Source: www.engineeringtoolbox.com

Preferably, a metal or metal alloy with a heat conductance of at least one of the values shown in the table of the metals are used for the metal members in the invention.

Metals used for the metal parts can be chosen between iron, nickel, aluminium, silver, gold, chromium, copper, platinum, brass, bronze, steel, stainless steel. An aluminium alloy is suitable for the heat sink 15, as it secures a high heat capacity versus weight ratio.

Pliable metal mesh can be woven metal lattice, braided metal or other kinds of metal webs.

The different metal parts in contact with each other, such as the metal elements 3, metal springs 12 and the heat sink 15 should be firmly attached to each other to secure a good heat transfer. Soldering, welding, rivets and thermal paste may be used.

| Reference signs: | |
|---|---|
| 1 | earpad |
| 2 | contact surface |
| 3 | metal element |
| 4 | earcup |
| 5 | earpad body |
| 6 | flexible cover layer |
| 7 | headset |
| 8 | headphone |
| 9 | ear defender |
| 10 | skin |
| 11 | holes |
| 12 | metal spring |
| 13 | metal balls |
| 14 | metal wool |
| 15 | heat sink |
| 16 | joint |
| 17 | thin layer of artificial leather |
| 18 | holes in leather layer |
| 19 | sponge or foam body |
| 20 | headband |
| 21 | neckband |
| 22 | microphone arm |
| 23 | microphone |
| 24 | cord |
| 25 | opening |
| 26 | ear |
| 27 | foam |
| 28 | outer part of metal element |
| 29 | inner part of metal element |
| 30 | intermediate part of metal element |
| 31 | braided metal fabric |
| 32 | base plate |
| 33 | copper mesh |

The invention claimed is:

1. A heat sinking earpad to provide an interface between an earcup of a headset or an ear defender, wherein the earpad comprises a contact surface contacting the skin of the ear or ear surrounding, wherein the earpad includes at least one heat conductive metal element, a metal heat conductor; and wherein at least one of the metal elements is in contact with the metal heat conductor so that heat is conducted away from the metal elements; and wherein the metal elements comprise a plurality of displaceable heat conducting metal balls.

2. The earpad according to claim 1 further including a flexible cover layer having a flexible heat conductive metal mesh therein.

3. The earpad according to claim 2, wherein the flexible cover layer includes a pliable metal foil.

4. The earpad according to claim 1, wherein the earpad body comprise metal wool.

5. The earpad according to claim 1, wherein the metal elements include a plurality of discrete freely displaceable elements confined by the flexible cover layer.

6. The earpad according to claim 2, wherein the flexible cover layer comprises a metal foil.

7. An earpad to provide an interface between an earcup of a headset or an ear defender, wherein the earpad comprises a contact surface contacting the skin of the ear or ear surrounding, wherein the earpad includes at least one metal element, a metal heat conductor; and wherein at least one of the metal elements is in contact with the metal heat conductor so that heat is conducted away from the metal elements, wherein the metal heat conductors include springs.

8. An earpad to provide an interface between an earcup of a headset or an ear defender, wherein the earpad comprises a contact surface contacting the skin of the ear, wherein the earpad includes at least one metal elements, a metal heat conductor; and wherein at least one of the metal elements comprises a plurality of displaceable metal balls and wherein at least one of said elements is in contact with the metal heat conductor so that heat is conducted away from the metal elements.

9. The earpad of claim 8 wherein said metal balls are generally immersed in a liquid.

10. An earpad to provide an interface between an earcup of a headset or an ear defender, wherein the earpad comprises a contact surface contacting the skin of the ear, wherein the earpad includes at least one metal elements, a metal heat conductor; and wherein at least one of the metal elements is in contact with the metal heat conductor so that heat is conducted away from the metal elements, and
further including a flexible cover layer having a flexible heat conductive metal mesh therein.

11. The earpad according to claim 6, wherein the flexible cover layer includes said pliable metal mesh.

12. An earpad to provide an interface between an earcup of a headset or an ear defender, wherein the earpad comprises a contact surface contacting the skin of the ear or ear surrounding, wherein the earpad includes at least one metal elements, a metal heat conductor; and wherein at least one of the metal elements is in contact with the metal heat conductor so that heat is conducted away from the metal elements, and
further including a flexible cover layer having a flexible heat conductive metal mesh therein; and
wherein the metal mesh on the contact surface is covered with a thin layer of material.

13. The earpad according to claim 10, wherein the earpad body comprise metal wool.

14. The earpad according to claim 9, wherein the flexible cover layer includes a liquid.

15. The earpad according to claim 9, wherein the earpad body includes a liquid.

16. An earpad according to claim 1, wherein the metal heat conductors include springs, which can be shortened, when a compressive force is added to the metal element.

17. An earpad according to claim 16, wherein the metal heat conductors are in contact with a metal heat sink, which dissipates heat into the surrounding air.

\* \* \* \* \*